(12) United States Patent
Willett, Jr. et al.

(10) Patent No.: US 8,746,049 B2
(45) Date of Patent: Jun. 10, 2014

(54) CREEP INDICATION SYSTEM AND METHOD FOR DETERMINING CREEP AMOUNT

(75) Inventors: Fred Thomas Willett, Jr., Burnt Hills, NY (US); Paul Stephen DiMascio, Greer, SC (US)

(73) Assignee: General Electric Company, Schenectady, NY (US)

( * ) Notice: Subject to any disclaimer, the term of this patent is extended or adjusted under 35 U.S.C. 154(b) by 337 days.

(21) Appl. No.: 13/225,776

(22) Filed: Sep. 6, 2011

(65) Prior Publication Data

US 2013/0058786 A1    Mar. 7, 2013

(51) Int. Cl.
  *G01M 15/00*  (2006.01)
  *G01N 11/00*  (2006.01)
  *G01N 9/24*   (2006.01)
  *G06F 11/30*  (2006.01)
  *G01L 3/00*   (2006.01)

(52) U.S. Cl.
  USPC ............ 73/112.01; 73/822; 73/602; 702/184; 702/41; 702/43

(58) Field of Classification Search
  USPC ......... 73/112.01, 602, 802; 702/33, 181, 184, 702/34
  See application file for complete search history.

(56) References Cited

U.S. PATENT DOCUMENTS

| | | | |
|---|---|---|---|
| 5,140,528 A | 8/1992 | Swaminathan et al. | |
| 6,568,254 B2 * | 5/2003 | Pross | 73/112.01 |
| 6,594,619 B1 | 7/2003 | von Flotow | |
| 6,785,635 B2 | 8/2004 | von Flotow | |
| 6,983,659 B2 * | 1/2006 | Soechting et al. | 73/802 |
| 7,328,620 B2 * | 2/2008 | Howard et al. | 73/602 |
| 7,493,809 B1 * | 2/2009 | Ward, Jr. | 73/168 |
| 7,503,218 B2 * | 3/2009 | Howard et al. | 73/602 |
| 7,552,647 B2 * | 6/2009 | Soechting et al. | 73/802 |
| 7,787,996 B2 * | 8/2010 | Draper et al. | 700/287 |
| 8,225,672 B2 * | 7/2012 | Arai et al. | 73/788 |
| 8,433,427 B2 * | 4/2013 | Glomann et al. | 700/30 |
| 2002/0019708 A1 * | 2/2002 | Pross | 702/36 |
| 2006/0201257 A1 * | 9/2006 | Soechting et al. | 73/802 |
| 2007/0285110 A1 * | 12/2007 | Nigmatulin et al. | 324/699 |
| 2009/0178417 A1 * | 7/2009 | Draper et al. | 60/783 |

\* cited by examiner

*Primary Examiner* — Lisa Caputo
*Assistant Examiner* — Jonathan Dunlap
(74) *Attorney, Agent, or Firm* — Dority & Manning, PA (57) ABSTRACT

A creep indication system and a method for determining a creep amount are disclosed. The system includes a first creep indicating member on a first rotating component and a second creep indicating member on a second rotating component. The second creep indicating member has at least one different creep characteristic from the first creep indicating member. The system further includes at least one measurement device configured to measure a change in radial position of at least one of the first creep indicating member or the second creep indicating member. The method includes measuring a first creep amount of a first creep indicating member and measuring a second creep amount of a second creep indicating member. The method further includes estimating a temperature of a rotating component using the first creep amount and the second creep amount.

19 Claims, 9 Drawing Sheets

CREEP INDICATION SYSTEM AND METHOD FOR DETERMINING CREEP AMOUNT

FIELD OF THE INVENTION

The present disclosure relates in general to rotating components, such as rotating components in turbine systems, and more particularly to systems and methods for determining a creep amount of the rotating components.

BACKGROUND OF THE INVENTION

Mechanical part life, such as of a rotor in a turbine, is dictated by one or more of several failure mechanisms. In turbine rotors subjected to high temperatures, creep and low cycle fatigue (LCF) are the prevalent failure mechanisms. Rotor failures can be catastrophic. A rotor burst can result in millions of dollars in damages and possibly loss of life. Consequently, rotors are designed for a useful life that is less than the predicted burst life, and is sufficiently less to greatly reduce the possibility of an in-service failure.

Many rotors have a limited creep life. Creep life prediction depends on many variables, including temperature, stress, and material properties. Stress can be monitored during turbine operation through rotor speed. Material properties, however, vary from rotor to rotor. Unfortunately, the range of material properties can only be determined through destructive testing. Because of the variability in material properties, rotor lives, both predicted and actual, vary widely. Additionally, temperature is typically difficult to measure. For example, it is typically prohibitively expensive and dangerous to attempt to mount a temperature measuring device to a rotor, because of the risk of the device becoming dislodged.

The extent of rotor creep can, for large rotors, be determined by measuring the rotor after a period of service. Typically, rotor diameter is measured, compared to the initial rotor diameter measurement, and correlated to a creep model to estimate the amount of creep, and hence the amount of life expended. Unfortunately, this approach requires good measurements of the new rotor, good data storage and retrieval, and disassembly of the turbine at the time of measurement. The disassembly requires expenditure of an extensive amount of time and costs.

Thus, an improved system and method for determining the creep of a rotating component, such as a rotor, is desired in the art.

BRIEF DESCRIPTION OF THE INVENTION

Aspects and advantages of the invention will be set forth in part in the following description, or may be obvious from the description, or may be learned through practice of the invention.

In one embodiment, a creep indication system is disclosed. The system includes a first creep indicating member on a first rotating component and a second creep indicating member on a second rotating component. The second creep indicating member has at least one different creep characteristic from the first creep indicating member. The system further includes at least one measurement device configured to measure a change in radial position of at least one of the first creep indicating member or the second creep indicating member.

In another embodiment, a method for determining a creep amount is disclosed. The method includes measuring a first creep amount of a first creep indicating member and measuring a second creep amount of a second creep indicating member. The second creep indicating member has at least one different creep characteristic from the first creep indicating member. The method further includes estimating a temperature of a rotating component using the first creep amount and the second creep amount.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Figure 1:
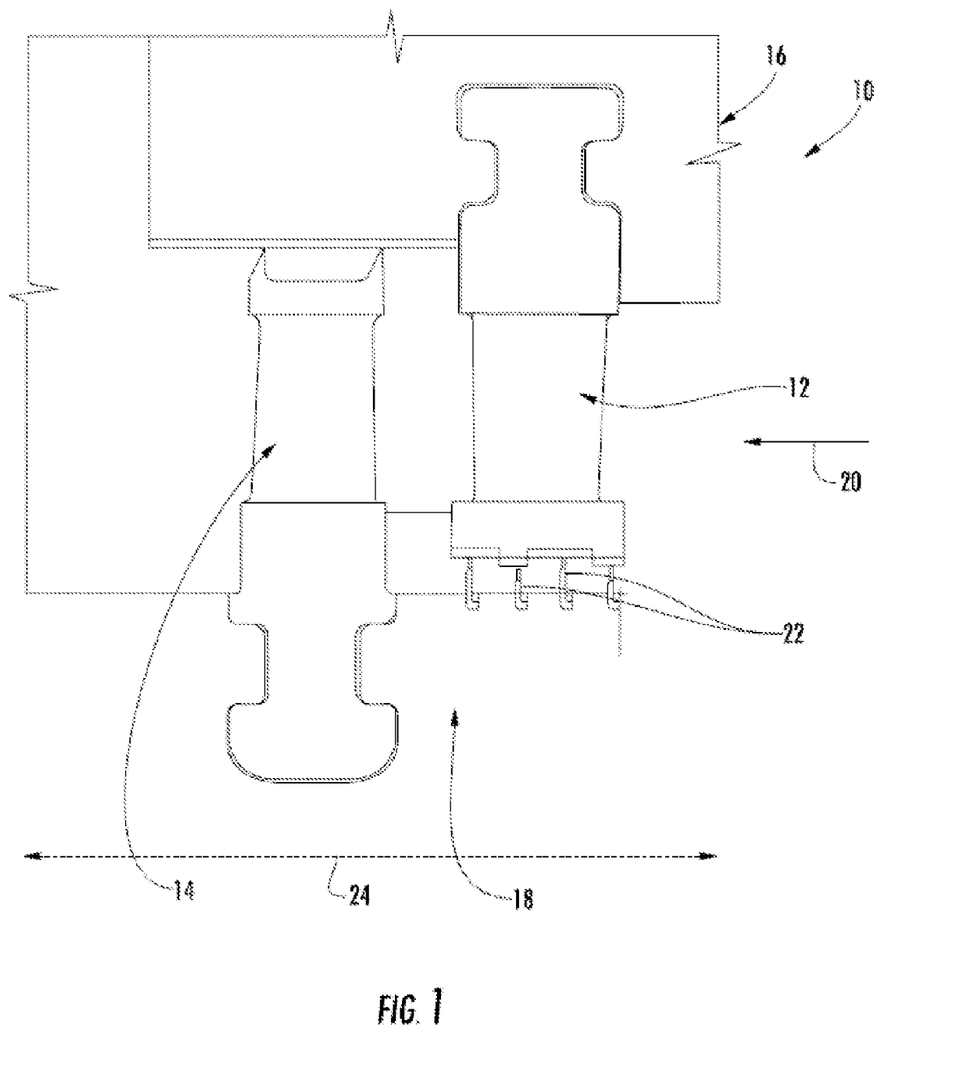
FIG. 1 is a sectional view of a portion of a turbine system according to one embodiment of the present disclosure.

FIG. 1 illustrates various components of a turbine system 10. The turbine system 10 may be, for example, a steam turbine system, a gas turbine system, or any other suitable turbine system. The various components illustrated in FIG. 1 may be components of, for example, a compressor or turbine of the turbine system 10.

The compressor and/or turbine may include one or more stages, such as one, two, three, four, five or more stages. Each stage may include a plurality of circumferentially spaced nozzles 12 and buckets 14 (one of each of which is illustrated in FIG. 1). The nozzles 12 may be circumferentially disposed within and connected to a shroud 16. The buckets 14 may be circumferentially disposed about and connected to a rotor wheel 18. Various sealing features may be provided in the stage to prevent the entrance and/or exit of various flows from the flow path 20 defined past the nozzles 12 and buckets 14. For example, in some embodiments, such as in steam turbines systems, a plurality of seals, such as J-seals 22, may be connected to the rotor wheel 18 to provide a seal between the rotor wheel 18 and nozzle 12.

As is generally known, various components of a compressor and/or turbine, such as of a stage as discussed above, may be generally movable components. The movable components are generally rotatable about a central axis 24, and are referred to herein as rotating components 30. For example, a bucket 14, a rotor wheel 18, and a seal, such as a J-seal 22, are examples of rotating components. However, it should be understood that the present disclosure is not limited to the above disclosed examples, and rather that any suitable rotating component is within the scope and spirit of the present disclosure.

Further, various of the rotating components 30 discussed herein may be referred to as first rotating components 32 and second rotating components 34. It should be understood that a first rotating component 32 and second rotating component 34 may be different rotating components 30, or may be the same rotating component 30. In some embodiments, the first and second rotating components 32 and 34 are rotating components within a single stage of a compressor or turbine of a turbine system 10.

As is generally known, various other components of a compressor and/or turbine, such as of a stage as discussed above, may be generally non-movable components. The non-movable components are referred to herein as stationary components 40. For example, a nozzle 12 and a shroud 16 are examples of stationary components. However, it should be understood that the present disclosure is not limited to the above disclosed examples, and rather that any suitable stationary component is within the scope and spirit of the present disclosure.

In many cases, it is desirable to determine a creep amount of a rotating component 30. Thus, the present disclosure is directed to a creep indication system 100. As shown in FIGS. 2, 3 and 5-12, the creep indication system 100 of the present disclosure includes a plurality of creep indicating members 110. The plurality of creep indicating members 110 includes at least one first creep indicating member 112 and at least one second creep indicating member 114. The first creep indicating member 112 is on a first rotating component 32, while the second creep indicating member 114 is on a second rotating component 34.

The second creep indicating member 114 has at least one different creep characteristic from the first creep indicating member 112. For example, in some embodiments, the second creep indicating member 114 has a different material from the material of the first creep indicating member 112. The creep indicating members 110 may be formed from any suitable materials, such as from metals or metal alloys. For example, the creep indicating members 110 may be formed from any suitable steel, nickel, nickel-based alloy, ferrous metal, ferrous-based alloy, nonferrous metal, nonferrous-based alloy, or any other suitable metal or metal alloys. In some embodiments, the first creep indicating member 112 may be formed from a relatively higher-grade steel while the second creep indicating member 114 may be formed from a relatively lower-grade steel, or vice versa. Alternatively, the first creep indicating member 112 may be formed from a steel while the second creep indicating member 114 is formed from a nickel-based alloy. Alternatively, the first creep indicating member 112 may be formed from any suitable material, while the second creep indicating member 114 is formed from any suitable material with different material characteristics.

Additionally or alternatively, the second creep indicating member 114 may have a different stress for other constant factors from the first creep indicating member 112, or may have any other suitable different creep characteristic, such as any suitable characteristic that causes the second creep indicating member 114 to have a different creep from the first creep indicating member 112.

As mentioned, each creep indicating member 110 is on a rotating component 30. As used herein, creep indicating member 110 may be "on" rotating component 30 by being integrally formed on a surface or in a surface of the rotating component 30, or by being coupled to the rotating component 30.

Creep indicating member 110 may in some embodiments be any structure configured to experience higher stress than rotating component 30, resulting in a greater creep rate than rotating component 30. That is, creep indicating member 110 may be designed such that it will creep faster than the rest of rotating component 30, so that its deflection is more pronounced and easier to measure. Alternatively, creep indicating member 110 may be any structure configured to experience lower stress or substantially identical stress as that of rotating component 30. Creep indicating member 110 may be configured in any of these fashions through the use of specific materials, shape, size, or other features. "Creep" as used herein indicates tendency of a solid material to slowly move or plastically deform under the influence of stresses and temperatures. Various embodiments of creep indicating member 110 will be described herein.

In some embodiments, the creep indication system 100 may further include at least one measurement device 120. Each measurement device 120 may be configured to measure a change in radial position of a creep indicating member 110. For example, in some embodiments, a first measurement device 122 may be configured to measure a change in radial position of the first creep indicating member 112, while a second measurement device 124 may be configured to measure a change in radial position of the second creep indicating member 114. Alternatively, a single measurement device 120 may be configured to measure changes in radial position of both the first and second creep indicating members 112 and 114.

Figure 3:
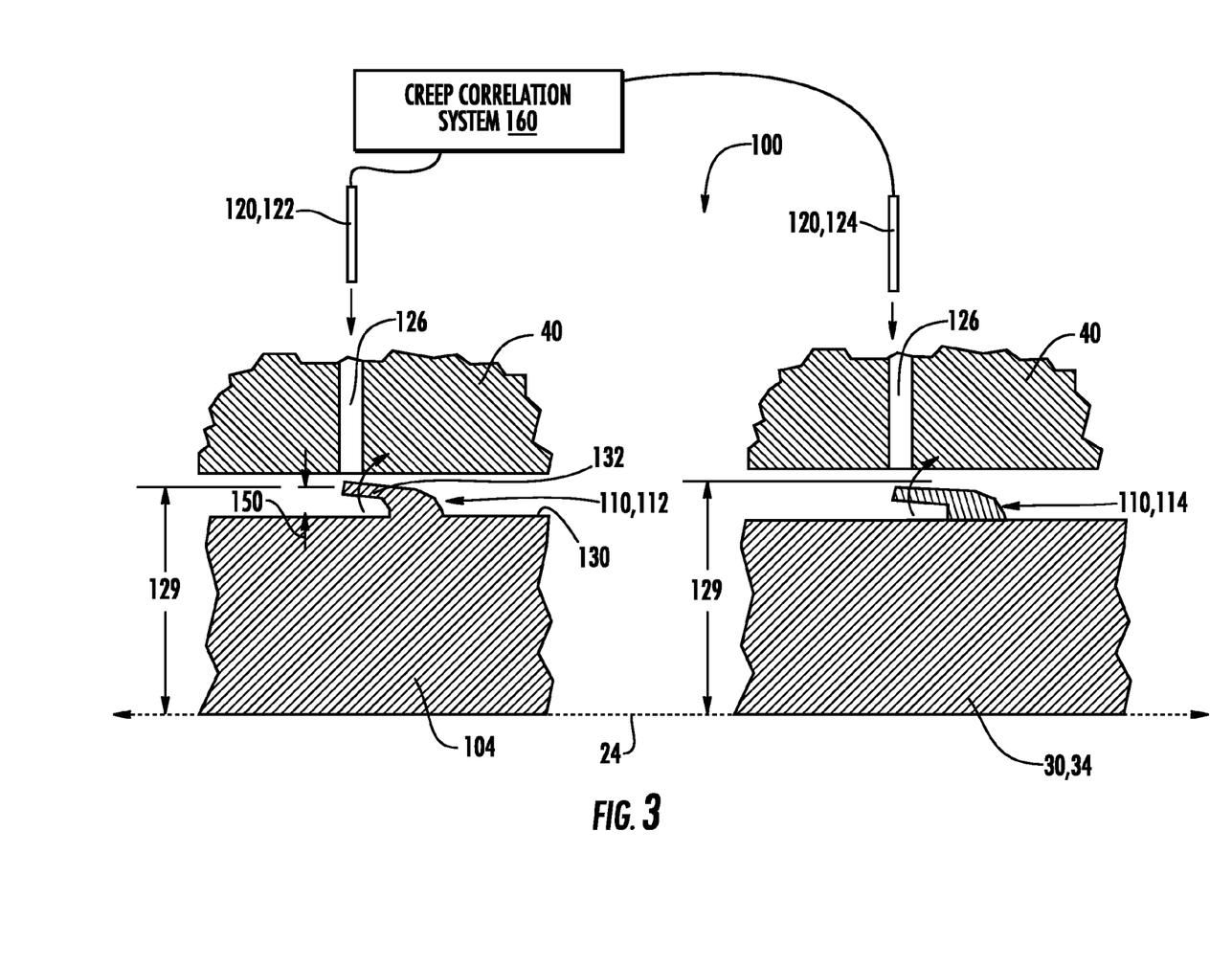
FIG. 3 shows a cross-sectional view of the system of FIG. 2 after a period of time of use.

FIG. 3 shows creep indicating member 112 and 114 after a period of time. In FIG. 3, creep indicating members 112 and 114 have been deformed radially outward. Measurement devices 122 and 124 are configured to measure radial positions of the creep indicating members 112 and 114, so as to provide an indication of life expectancy of rotating component 104. For example, initial radial position 127 may be subtracted from radial position 129 after a period of time to determine a change in radial position. As will be described herein, a measurement device 120 may extend through a port 126 in a stationary component 40, or may otherwise be allowed to measure a radial position of a creep indicating member 110. Numerous embodiments of measurement device 120 will also be described herein.

Figure 4:
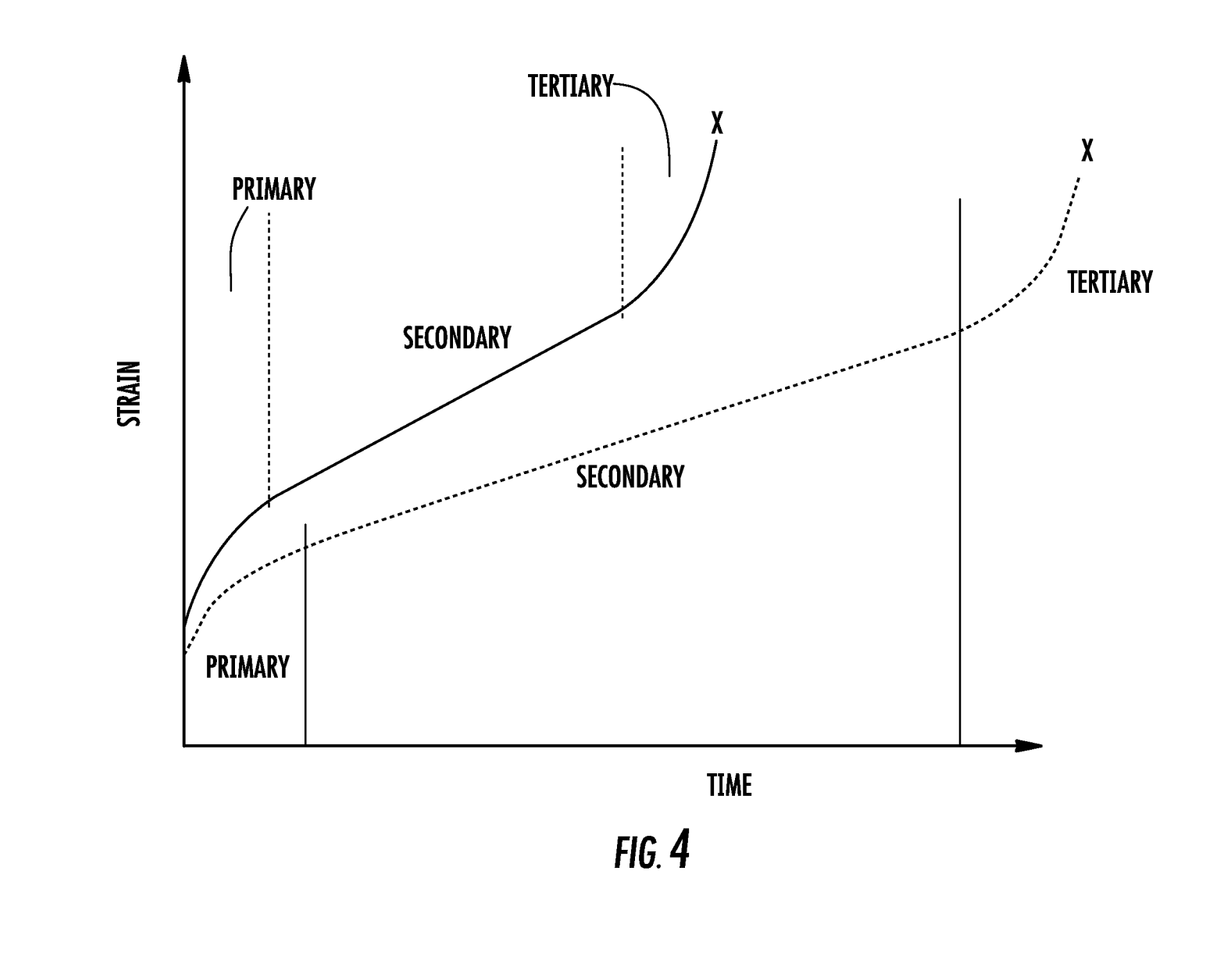
FIG. 4 shows a graph indicating creep of a rotating component versus a creep indicating member for use with a creep correlation system according to one embodiment of the present disclosure.

To illustrate how system 100 indicates life expenditure, deformation and/or impending mechanical failure of rotating component 30, FIG. 4 shows a graph of strain versus time. In FIG. 4, the dashed line indicates strain over time in a portion of rotating component 30, while the solid line shows strain over time of creep indicating member 110. Since creep indicating member 110 in the embodiment shown in FIG. 4 is more highly stressed, e.g., due to its shape, it creeps faster. Deformation of creep indicating member 110 radially outward as rotating component 30 rotates can be correlated to deformation in rotating component 30, e.g., using conventional modeling. In this fashion, creep indicating member 110 provides an indication of deformation in, and hence life expectancy of, rotating component 30 without having to actually measure rotating component 30.

Figure 2:
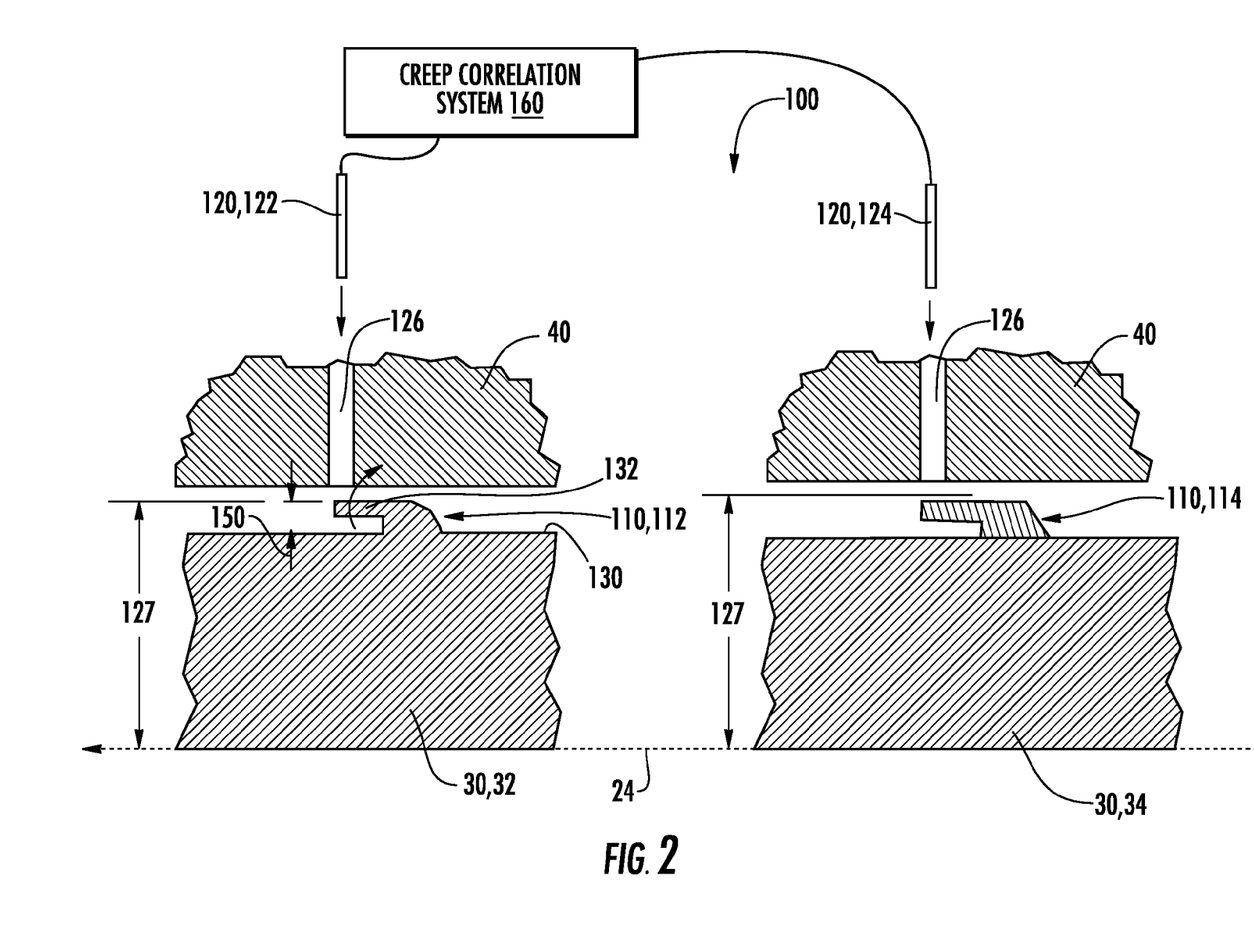
FIG. 2 shows a cross-sectional view of a creep indication system including a first creep indicating member and a second creep indicating member according to one embodiment of the present disclosure.

Creep indicating member 110 may take a variety of forms. In FIGS. 2 and 3, creep indicating member 110 is integrally formed on rotating component 104. That is, creep indicating member 110 includes an additional amount of material on a surface 130 of rotating component 30 such that it extends radially beyond surface 130 of rotating component 30. In FIGS. 2 and 3, creep indicating member 110 includes a cantilevered element 132 that initially extends substantially parallel to central axis 24 of rotating component 30. In this embodiment, cantilevered element 132 extends radially beyond surface 130 of rotating component 30. As rotating component 30 rotates over time, as shown by the curved arrow in FIG. 2, cantilever element 132 bends or deflects radially outwardly from initial radial position 127 to new radial position 129, as shown in FIG. 3. The cantilever design of creep indicating member 110 exaggerates the deflection for a given amount of creep strain, making measurement easier. Creep indicating member 110 may be formed in any manner now known or later developed. For example, it may be incorporated into the forging for rotating component 30, machined from a forging along with surface 130, or welded to rotating component 30 either in finished form or with machining to shape being provided thereafter.

Figure 5:
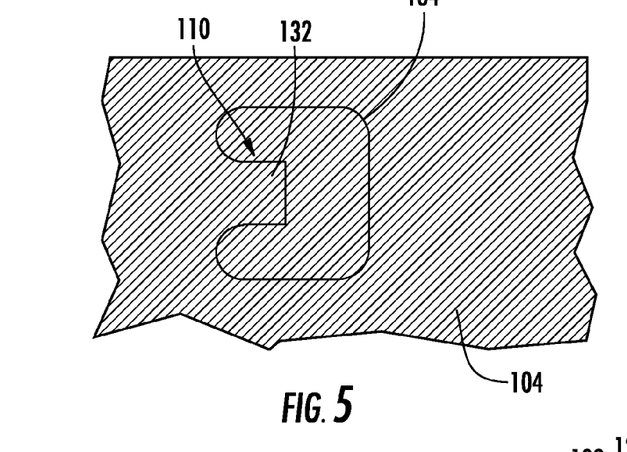
FIG. 5 shows a plan view of a creep indicating member according to another embodiment of the present disclosure.
Figure 6:
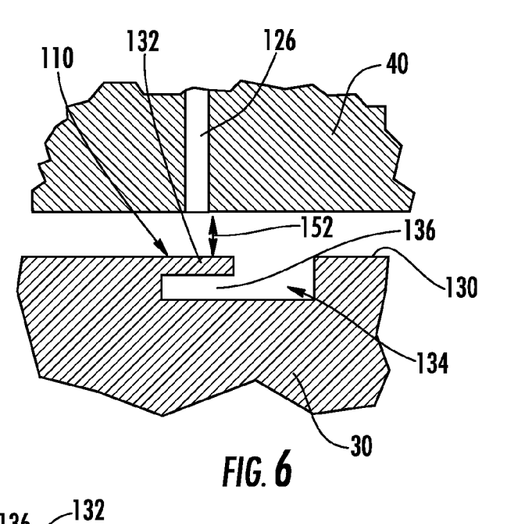
FIG. 6 shows a cross-sectional view of the creep indicating member of FIG. 5.
Figure 7:
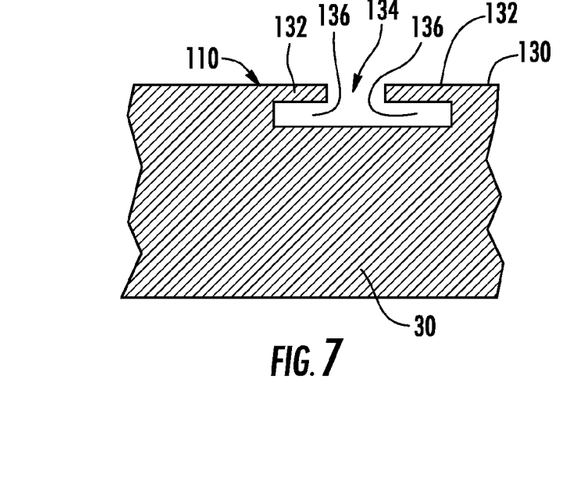
FIG. 7 shows a cross-sectional view of a creep indicating member according to another embodiment of the present disclosure.

As shown in FIGS. 5-7, in an alternative embodiment, a creep indicating member 110 may be formed in rotating component 30. In this embodiment, creep indicating member 110 includes a cantilevered element 132 that is initially substantially flush with surface 130 (FIGS. 5 and 6) of rotating component 30. Cantilevered element 132 may be formed by machining an opening 134 in a rotating component 30 in any now known or later developed manner. Opening 134 includes an undercut 136 to form cantilevered element 132. As shown in FIG. 7, in an alternative embodiment, cantilevered element 132 may include a pair of longitudinally opposed cantilevered elements 132, e.g., by having opening 134 include a pair of undercuts 136.

Figure 8:
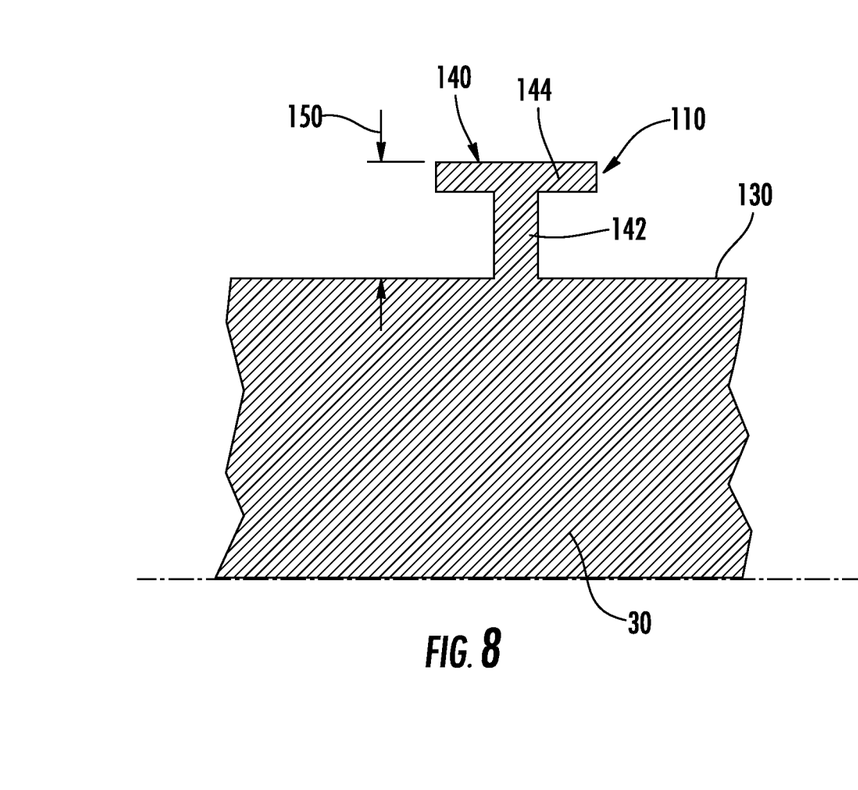
FIG. 8 shows a cross-sectional view of a creep indicating member according to another embodiment of the present disclosure.
Figure 9:
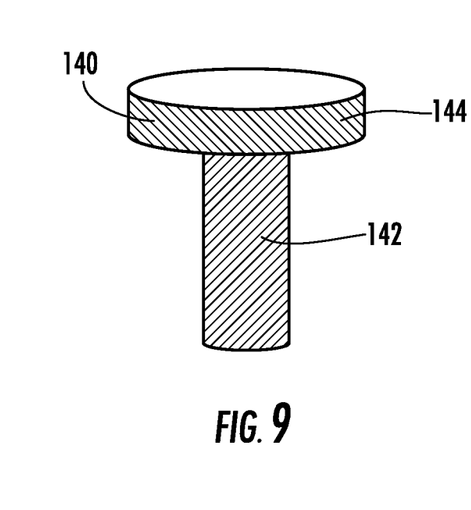
FIG. 9 shows a perspective view of the creep indicating member of FIG. 8.

FIGS. 8 and 9 show another alternative embodiment in which a creep indicating member 110 includes a pinhead-shaped element 140 extending from surface 130 of rotating component 30. Pinhead-shaped element 140 may include, for example, a stem 142 and, optionally, a flattened head 144. Creep indicating member 110 may be provided on rotating component 30 in any fashion, as described above. Stem 142 as shown is under a substantially pure tensile load (rather than a bending load as in other embodiments) and creeps over time. Flattened head 144 may provide added weight to increase the centrifugal pull on stem 142.

Figure 10:
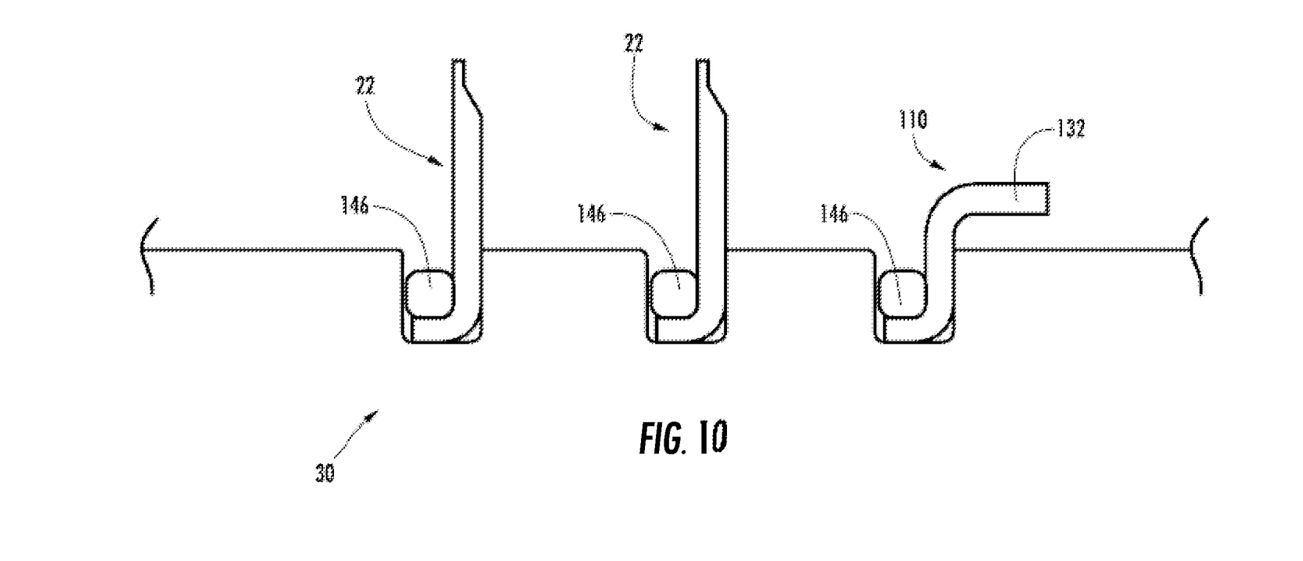
FIG. 10 shows a cross-sectional view of a creep indication system including a creep indicating member according to one embodiment of the present disclosure.

FIG. 10 shows another alternative embodiment of a creep indicating member 110. In these embodiments, the creep indicating member 110 may replace a seal in the system 10, such as a J-seal 22. The creep indicating member 110 may include a cantilevered element 132, as shown, and/or a stem 142, and/or other suitable components as discussed above. The creep indicating member 110 in these embodiments may be coupled to the rotating component 30, as shown, such as in the same manner that a seal is coupled to the rotating component 30. For example, a coupling member 146, which may press-fit the creep indicating member 110 to the rotating component 30, or a suitable adhesive or mechanical fastener or other suitable coupling device or method may be utilized.

In some embodiments, each creep indicating member 110 is present at only a portion of the circumference of rotating component 30. In these cases, multiple local creep indicating members 110 may be arranged circumferentially spaced about rotating component 30 to provide proper balance of rotating component 30. In alternative embodiments, however, a creep indicating member 110 may extend about an entire circumference of rotating component 30. In this latter case, no rotating component 104 imbalance is presented.

It should be understood that the creep indicating members according to the present disclosure may be applied to newly manufactured rotating components 30, or can be applied, such as retrofitted, to existing rotating components 30. Further, it is emphasized that the creep indicating members 110 described herein may additionally or alternatively include a variety of other suitably shapes not described herein capable of changing radial position over time.

Figure 11:
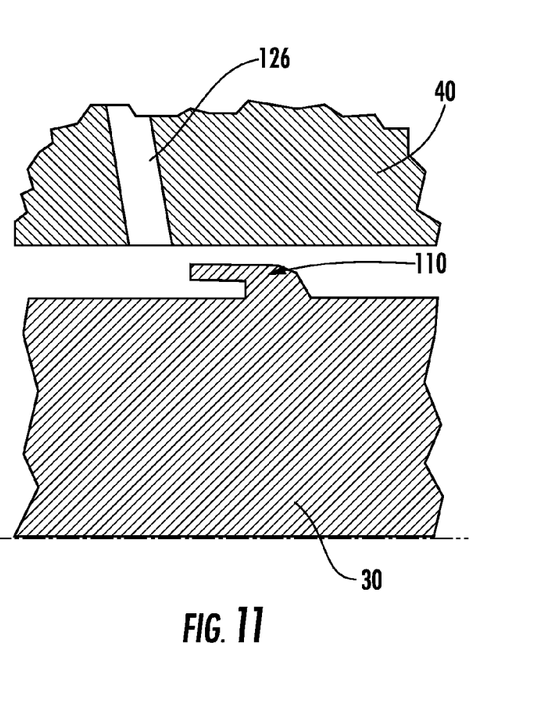
FIG. 11 shows a cross-sectional view of a creep indication system including a creep indicating member according to another embodiment of the present disclosure.
Figure 12:
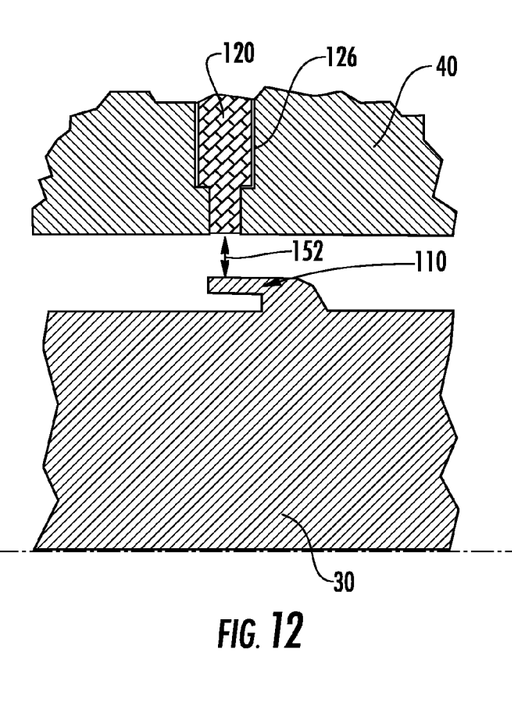
FIG. 12 shows a cross-sectional view of a creep indication system including a creep indicating member according to another embodiment of the present disclosure.

Referring to FIGS. 2 and 3, along with FIGS. 11 and 12, measurement device 120 may include a variety of devices capable of measuring or detecting the change in radial position of creep indicating member 110. In some embodiments, rotating component 30 does not need to be removed from its location, e.g., within stationary component 40, in order to determine life expenditure, deformation, etc., of rotating component 30. As noted herein, measurement device 120 may be provided through port 126 in stator 40. Port 126 may open radially outward of creep indicating member 110, as shown in FIGS. 2, 3, 6 and 12. In this case, measurement device 120 may include, for example, a dial indicator or laser measurement device. Alternatively, port 126 may open to creep indicating member 110 at an angle, as shown in FIG. 11. In this case, measurement device 120 may include a borescope, which may also be employed for visual inspection. In some embodiments, such as where measurement device 120 includes a clearance sensor, it may be possible to make the measurement during operative rotation of rotating component 30. Decreasing clearance between creep indicating member 110 and stationary component 40 would indicate creep. In these cases, the turbine system 10 would not need to be stopped.

Measurement of the change in radial position (new radial position 129 minus initial radial position 127) can be accomplished in a number of ways. Measuring a creep distance 150 as shown in, for example, FIGS. 2 and 8, is one approach. Another approach is to measure the change in clearance distance 152, as shown in FIG. 6, between creep indicating member 210 on rotating component 30 and stationary component 40. In some embodiments, clearance distance 152 can be measured continuously when system 10 is operating. In this fashion, a decrease in clearance distance over time can be correlated to creep strain, and hence rotating component 30 life expenditure.

Referring again to FIGS. 2 and 3, creep indication system 100 may also include a creep correlation system 160 configured to correlate a creep amount of a creep indicating member 110, or of at least one of first creep indicating member 112 or second creep indicating member 114, to a creep amount of a rotating component 30, or of at least one of first rotating component 32 or second rotating component 34. Creep correlation system 160 may employ any now known or later developed predictive, computerized models. In some embodiments, creep correlation system 160 may correlate an expected creep amount for a rotating component 30 with a creep indicating member 110 based on, for example, expected materials, known size, known operating environment, temperature, etc.

Figure 13:
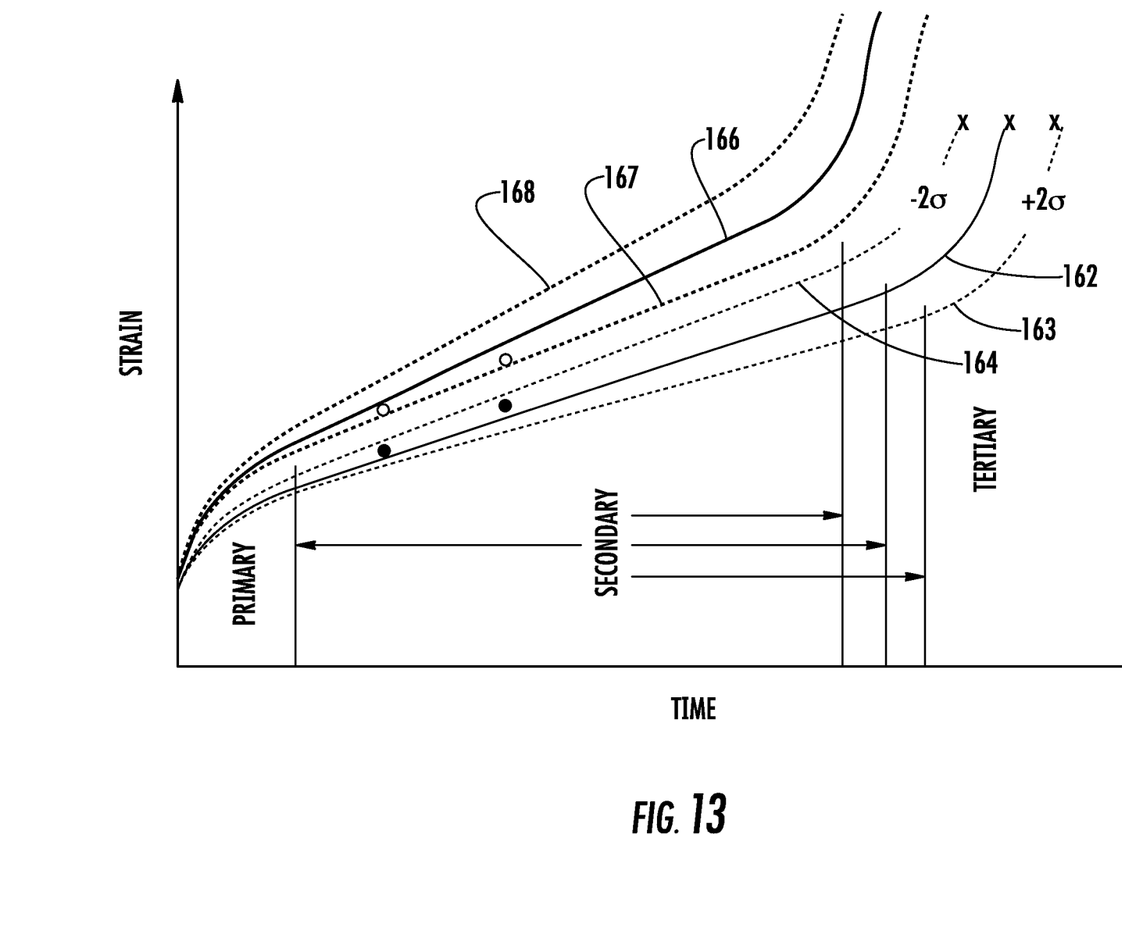
FIG. 13 shows a graph indicating modeling of creep for a first creep indicating member and a second creep indicating member for use with a creep correlation system according to one embodiment of the present disclosure.

Referring now to FIG. 13, solid curve 162 represents the average creep properties of a first material. The material may be that of a creep indicating member 110, such as of first creep indicating member 112, and/or a rotating component 30, such as first rotating component 32. The dashed curves 163 and 164 represent the range of creep property uncertainty, defined in this example as +/−two standard deviations (±2σ). The properties of any creep indicating member 110 and/or rotating component 30 of the given material lies somewhere in the continuum bounded by the range of uncertainty. By measuring the creep deformation in a creep indicating member 110 formed of the same material of a rotating component 30 that has been added to the rotating component 30 at points in time, the rate of deformation thereof can be determined. With this measured rate of deformation of the added creep indicating member 110, creep correlation system 160 can establish creep properties for the particular rotating component 30 and estimate an expended life using any now known or later developed modeling technique.

Still referring to FIG. 13, solid curve 166 represents the average creep properties of a second material. The material may be that of a creep indicating member 110, such as of second creep indicating member 114, and/or a rotating component 30, such as second rotating component 34. The dashed curves 167 and 168 represent the range of creep property uncertainty, defined in this example as +/−two standard deviations (±2σ). The properties of any creep indicating member 110 and/or rotating component 30 of the given material lies somewhere in the continuum bounded by the range of uncertainty, as discussed above.

By measuring the creep amount of both the first material and second material, various common characteristics of the first material and second material, such as temperature of the materials during operation, can be estimated. For example, after measuring a creep amount at two points in time for each material, these results may be utilized to estimate temperature by determining the range of temperatures that would produce a given creep amount for a given time period for the first material while also producing a given creep amount for a given time period for the second material. The estimated temperature or range of temperatures, or other determined common characteristic, may then be input into creep correlation system 160, which may allow the correlation system 160 to more accurately correlate a creep amount of a rotating component 30.

The present disclosure is further directed to a method for determining a creep amount in a turbine system 10. The method includes measuring a first creep amount of a first creep indicating member 112 and measuring a second creep amount of a second creep indicating member 114, as discussed above. The method further includes estimating a temperature of a rotating component 30, such as a first rotating component 32 or second rotating component 34, using the first creep amount and the second creep amount, as discussed above. In some embodiments, the method further includes correlating at least one of the first creep amount or the second creep amount to a creep amount of the rotating component 30, as discussed above.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A creep indication system, the system comprising:
a first creep indicating member on a first rotating component;
a second creep indicating member on a second rotating component, the second creep indicating member having at least one different creep characteristic from the first creep indicating member,
wherein the first creep indicating member and the second creep indicating member each includes a cantilevered element initially extending substantially parallel to a longitudinal axis of the respective first rotating component and second rotating component; and
at least one measurement device configured to measure a change in radial position of at least one of the first creep indicating member or the second creep indicating member.

2. The creep indication system of claim 1, wherein the at least one different creep characteristic is a different material.

3. The creep indication system of claim 1, wherein the first rotating component and the second rotating component are the same component.

4. The creep indication system of claim 1, further comprising a plurality of measurement devices, the plurality of measurement devices comprising a first measurement device configured to measure a change in radial position of the first creep indicating member and a second measurement device configured to measure a change in radial position of the second creep indicating member.

5. The creep indication system of claim 1, wherein the first creep indicating member is integrally formed on the first rotating component and the second creep indicating member is coupled to the second rotating component.

6. The creep indication system of claim 1, further comprising a creep correlation system configured to correlate a creep amount of at least one of the first creep indicating member or the second creep indicating member to a creep amount of at least one of the first rotating component or the second rotating component.

7. The creep indication system of claim 1, wherein the first creep indicating member and the second creep indicating member are configured to experience higher stress than the respective first rotating component and second rotating component.

8. The creep indication system of claim 1, wherein the first creep indicating member and the second creep indicating member are each formed from one of a metal or metal alloy.

9. A method for determining a creep amount, the method comprising:
- measuring a first creep amount of a first creep indicating member;
- measuring a second creep amount of a second creep indicating member, the second creep indicating member having at least one different creep characteristic from the first creep indicating member; and
- estimating a temperature of a rotating component using the first creep amount and the second creep amount.

10. The method of claim 9, further comprising correlating at least one of the first creep amount or the second creep amount to a creep amount of the rotating component.

11. The method of claim 9, wherein the at least one different creep characteristic is a different material.

12. The method of claim 9, wherein the first rotating component and the second rotating component are the same component.

13. The method of claim 9, wherein the first creep indicating member is on a first rotating component and the second creep indicating member is on a second rotating component, and wherein the estimating step comprises estimating a temperature of at least one of the first rotating component or the second rotating component.

14. The method of claim 13, wherein the first rotating component and the second rotating component are the same component.

15. A turbine system comprising:
- a first rotating component;
- a second rotating component;
- a first creep indicating member on the first rotating component;
- a second creep indicating member on the second rotating component, the second creep indicating member having at least one different creep characteristic from the first creep indicating member; and
- at least one measurement device configured to measure a change in radial position of the first creep indicating member and the second creep indicating member; and
- a creep correlation system configured to estimate a temperature of one of the first rotating component or the second rotating component using the change in radial position of the first creep indicating member and the second creep indicating member.

16. The turbine system of claim 15, wherein the at least one different creep characteristic is a different material.

17. The turbine system of claim 15, wherein the first rotating component and the second rotating component are the same component.

18. The turbine system of claim 15, wherein the creep correlation system is configured to correlate a creep amount of at least one of the first creep indicating member or the second creep indicating member to a creep amount of at least one of the first rotating component or the second rotating component.

19. The turbine system of claim 15, wherein the first creep indicating member and the second creep indicating member are configured to experience higher stress than the respective first rotating component and second rotating component.

* * * * *